United States Patent [19]

Kioka et al.

[11] Patent Number: 4,952,540

[45] Date of Patent: Aug. 28, 1990

[54] FINELY DIVIDED ALUMINOXANE, PROCESS FOR PRODUCING SAME AND ITS USE

[75] Inventors: Mamoru Kioka; Norio Kashiwa, both of Iwakuni, Japan

[73] Assignee: Mitsui Petrochemical Industries, Ltd., Tokyo, Japan

[21] Appl. No.: 155,075

[22] Filed: Feb. 11, 1988

[30] Foreign Application Priority Data

Feb. 14, 1987 [JP] Japan .................. 62-31926

[51] Int. Cl.$^5$ ........................ C08F 4/64; B01J 31/14
[52] U.S. Cl. ........................................ 502/9; 502/8; 502/103; 502/113; 502/117; 502/152
[58] Field of Search .............. 502/8, 9, 103, 113, 502/117, 152

[56] References Cited

U.S. PATENT DOCUMENTS

| | | | |
|---|---|---|---|
| 3,231,550 | 1/1966 | Manyik et al. | 502/117 X |
| 4,055,510 | 10/1977 | Peska et al. | 502/8 X |
| 4,293,673 | 10/1981 | Hamer et al. | 502/9 X |
| 4,311,817 | 1/1982 | Morita et al. | 502/9 X |
| 4,404,344 | 9/1983 | Sinn et al. | 502/117 X |
| 4,410,672 | 10/1983 | Inazawa | 502/117 X |
| 4,424,138 | 1/1984 | Candlin et al. | 502/9 |
| 4,530,914 | 7/1985 | Ewen et al. | 502/117 X |

FOREIGN PATENT DOCUMENTS 0206794 12/1986 European Pat. Off. .

*Primary Examiner*—Patrick P. Garvin
*Attorney, Agent, or Firm*—Sherman and Shalloway

[57] ABSTRACT

A finely divided aluminoxane comprising an aluminoxane represented by formula [I] or [II]

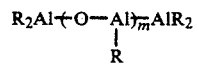

[I]

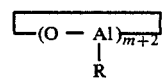

[II]

wherein R denotes a hydrocarbon group having 1 to 10 carbon atoms and m denotes an integer of 2 to 50, an average particle size being 5 to 200 $\mu$m and a specific an average particle size being 5 to 200 $\mu$m and a specific surface area being 20 to 1000 m$^2$/g, a process for producing same, and a catalyst component for polymerization of olefins being said finely divided aluminoxane.

32 Claims, No Drawings

FINELY DIVIDED ALUMINOXANE, PROCESS FOR PRODUCING SAME AND ITS USE

FIELD OF THE INVENTION

This invention relates to a finely divided aluminoxane, a process for producing same and its use. More specifically, this invention relates to a finely divided aluminoxane having a large specific surface area, and further to a catalyst component for polymerization of olefins being a finely divided aluminoxane that can form a catalyst having a remarkable olefin polymerization activity in combination with a catalyst component of a compound of a transition metal of Group IVB in the periodic table, and a process for producing same.

PRIOR ART

As a process for polymerizing alpha-olefins, there has been hitherto known a process in which ethylene and an alpha-olefin are copolymerized in the presence of a titanium compound-type catalyst composed of a titanium compound and an organoaluminum compound or a vanadium compound-type catalyst composed of a vanadium compound and an organoaluminum compound. Generally, ethylene/alpha-olefin copolymers obtained by using the titanium-type catalyst have been wide in molecular weight distribution and composition distribution and poor in transparency, surface non-tackiness and dynamic properties. Moreover, ethylene/alpha-olefin copolymers obtained by using the vanadium-type catalyst have become fairly narrow in molecular weight distribution and composition distribution and quite improved in transparency, surface non-tackiness and dynamic properties compared to the ethylene/alpha-olefin copolymers formed by using the titanium-type catalyst. However, the latter copolymers are still insufficient in usage requiring these properties, and alpha-olefin polymers, above all, ethylene/alpha-olefin copolymers having more improved properties have been demanded. Besides owing to low polymerization activity, a large amount of the catalyst remains in the resulting polymers, and a so-called ash removal step of removing the catalyst component from the polymers is needed.

Meanwhile, a catalyst composed of a zirconium compound and an aluminoxane has been lately proposed as a new Ziegler-type olefin polymerization catalyst.

Japanese Laid-open Patent Application No. 19,309/1983 describes a process wherein ethylene and one or more kinds of $C_3$–$C_{12}$ alpha-olefins are polymerized at a temperature of $-50°$ C. to $20°$ C. in the presence of a catalyst composed of a transition metal compound represented by formula (cyclopentadienyl)$_2$Me R Hal wherein R denotes cyclopentadienyl, $C_1$–$C_6$ alkyl or halogen, Me denotes a transition metal and Hal denotes halogen, and a linear aluminoxane represented by formula Al$_2$OR$_4$(Al(R)—O)$_n$ wherein R denotes methyl or ethyl and n denotes a number of 4 to 20, or
a cyclic aluminoxane represented by formula

wherein R and n are as defined above. Said Japanese Laid-open Patent Application indicates that to adjust a density of the obtained polyethylene, ethylene has to be polymerized in the presence of as small as up to 10% by weight of an alpha-olefin or its mixture.

Japanese Laid-open Patent Application No. 95,292/1984 describes a process for producing a linear aluminoxane represented by formula

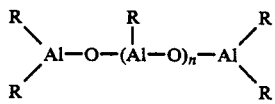

wherein n denotes 2 to 40 and R denotes $C_1$–$C_6$ alkyl, and
a cyclic aluminoxane represented by formula

wherein n and R are as defined above. Said Japanese Laid-open Patent Application mentions that when an olefin is polymerized in the presence of a mixture of e.g. methylaluminoxane produced by the above process and a bis(cyclopentadienyl) compound of titanium or zirconium, more than 25,000,000 g, per gram of a transition metal, of polyethylene is obtained for one hour.

Japanese Laid-open Patent Application No. 35,005/1985 discloses a process for producing a catalyst acting an aluminoxane compound represented by formula

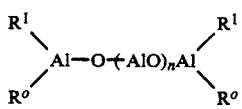

wherein $R^1$ denotes $C_1$–$C_{10}$ alkyl, $R^o$ is $R^1$ or together with $R^1$, denotes —O—,
with a magnesium compound, then chlorinating the reaction mixture, and further treating the chlorinated substance with a compound of Ti, V, Zr or Cr. In said Japanese Laid-open Patent Application, it is stated that the above catalyst is most suited to copolymerize ethylene with a $C_3$–$C_{12}$ alpha-olefin.

Japanese Laid-open Patent Application No. 35,006/1985 discloses a combination of (a) two or more different types of mono-, di- and tri-cyclopentadienyls or their derivatives of transition metals and (b) aluminoxanes as a catalyst for preparation of blend polymers. Example 1 of said Japanese Laid-open Patent Application shows that ethylene and propylene are polymerized in the presence of a catalyst composed of bis(pentamethylcyclopentadienyl)zirconiumdimethyl and an aluminoxane to provide polyethylene having a number-average molecular weight of 15,300, a weight-average molecular weight of 36,400 and a propylene content of 3.4%. In Example 2 of same, ethylene and propylene are polymerized in the presence of a catalyst composed of bis(methylcyclopentadienyl)zirconium dichloride and an aluminoxane to afford a blend of polyethylene and an ethylene/propylene copolymer consisting of a toluene-soluble portion having a number-average molecular weight of 2,200 and a weight-average molecular weight of 11,900 and containing 30 mole % of a propylene component and a toluene-insoluble portion having a number-average molecular weight of 3,000 and a weight-average molecular weight of 7,400 and containing 4.8 mole % of a propylene component, said blend having a number-average molecular weight of 2,000 and a weight-average molecular weight of 8,300 and containing 7.1 mole % of a propylene component. Example 3 of same indicates a blend of LLDPE and an ethylene-propylene copolymer consisting of a soluble portion having a molecular weight distribution (Mw/Mn) of 4.57 and containing 20.6 mole % of a propylene component and an insoluble portion having a molecular weight distribution of 3.04 and containing 2.9 mole % of a propylene component.

Japanese Laid-open Patent Application No. 35,007/1985 involves a process wherein ethylene alone is polymerized or ethylene and an alpha-olefin having 3 or more carbon atoms are copolymerized in the presence of a catalyst composed of metallocene and a cyclic aluminoxane represented by formula

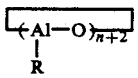

wherein R denotes an alkyl group having 1 to 5 carbon atoms and n denotes an integer of 1 to about 20, or
a linear aluminoxane represented by formula

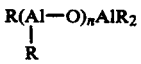

wherein R and n are as defined above. The polymer yielded by the above process is described to have a weight-average molecular weight of about 5,000,000 to about 1,400,000 and a molecular weight distribution of 1.5 to 4.0.

Japanese Laid-open Patent Application 35,008/85 mentions that polyethylene or an ethylene/$C_3$-$C_{10}$ alpha-olefin having a wide molecular weight distribution is produced by using a catalyst system composed of at least two metallocenes and aluminoxane, stating that the copolymer has a molecular weight distribution (Mw/Mn) of 2-50.

The catalysts formed from the transition metal compounds and aluminoxanes which are proposed in these prior technologies have markedly excellent polymerization activity compared to hitherto known catalyst systems composed of transition metal compounds and organoaluminum compounds. However, most of the catalyst systems proposed there are soluble in a reaction system and mainly used in solution polymerization; thus, a process is limited. Besides, when a polymer having a high molecular weight is produced, a solution viscosity of the polymerization system goes quite high inconveniently, and a bulk specific gravity of the polymer obtained by the post treatment of the solution system is low, making it hard to form a polymer having excellent properties as powder.

On the other hand, an attempt has been made to polymerize olefins by suspension polymerization or gaseous phase polymerization using a catalyst wherein one or both of the aforesaid transition metal compounds and aluminoxanes are supported on carriers of porous inorganic oxides such as silica, silica/alumina and alumina.

For example, said Japanese Laid-open Patent Applications Nos. 35,006/1985, 35,007/1985 and 35,008/1985 describe the use of the catalyst wherein the transition metal compounds and aluminoxanes are supported on silica, silica/alumina or alumina.

Japanese Laid-open Patent Applications Nos. 106,808/1985 and 106,809/1985 propose a process for producing a composition composed of a polyethylene-type polymer and a filler formed by polymerizing ethylene or copolymerizing ethylene with an alpha-olefin in the presence of a substance obtained by previously contacting a highly active catalyst component containing titanium and/or zirconium and soluble in a hydrocarbon solvent and a filler, an organoaluminum compound and a filler having an affinity for polyolefins.

Japanese Laid-open Patent Application No. 31,404/1986 proposes a process for polymerizing ethylene or copolymerizing ethylene with an alpha-olefin in the presence of a catalyst mixture composed of a product obtained by reacting a trialkylaluminum with water in the presence of silicon dioxide and aluminum oxide, and a transition metal compound.

Japanese Laid-open Patent Application No. 276,805/1986 proposes a process for polymerizing an olefin in the presence of a catalyst composed of a zirconium compound and a reaction mixture obtained by reacting a reaction mixture of an aluminoxane and trialkylaluminum with an inorganic oxide having a surface hydroxyl group such as silica.

Japanese Laid-open Patent Application No. 108,610/1981 proposes a process for polymerizing ethylene or copolymerizing ethylene with an alpha-olefin in the presence of a catalyst mixture composed of a product obtained by reacting a trialkylaluminum with water in the presence of silicon dioxide and aluminum oxide, and a transition metal compound.

However, even if olefins are polymerized or copolymerized by suspension polymerization or gaseous phase polymerization using the carrier supported solid catalyst components proposed in these prior technologies, the polymerization activity heavily decreases in comparison to the aforesaid solution polymerization, characteristics inherent in the catalyst composed of the transition metal compound catalyst component and the aluminoxane catalyst component are not exhibited enough, and properties as a powder, e.g. a bulk specific gravity, of the resulting polymer are also insufficient. Moreover, because the inorganic compounds used as the carriers have high melting points, they are at times observed in the polymer as appreciable foreign matters, impairing the appearance of films or decreasing the strength of films, for example.

SUMMARY OF THE INVENTION

It is an object of this invention to provide a finely divided aluminoxane having a large specific surface area and a uniform particle size, and more specifically to provide a catalyst component for polymerization of olefins being a finely divided aluminoxane that can form a catalyst having a high olefin polymerization activity in combination with a catalyst component of a compound of a transition metal of Group IVB in the periodic table.

Another object of this invention is to provide a process for producing a finely divided aluminoxane having a large specific surface area and a uniform particle size.

According to this invention, the above objects are achieved by a finely divided aluminoxane comprising an aluminoxane represented by formula [I] or [II]

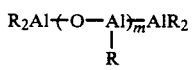

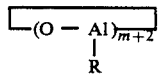

wherein R denotes a hydrocarbon group having 1 to 10 carbon atoms and m denotes an integer of 2 to 50,
and having an average particle size of 5 to 200 μm and a specific surface area of 20 to 1,000 m²/g.

Further, according to this invention, the above objects are achieved by a process for producing a finely divided aluminoxane which comprises contacting a solution of an aluminoxane represented by formula [I] or [II]

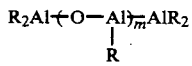

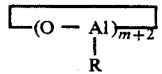

wherein R denotes a hydrocarbon group having 1 to 10 carbon atoms and m denotes an integer of 2 to 50,
with an aluminoxane-insoluble or -sparingly soluble solvent to precipitate a finely divided solid aluminoxane in suspension, and a process for producing a finely divided aluminoxane which comprises spray drying a solution of an aluminoxane represented by formula [I] or [II]

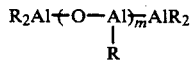

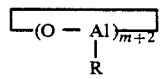

wherein R denotes a hydrocarbon group having 1 to 10 carbon atoms and m denotes an integer of 2 to 50,
to form a finely divided solid aluminoxane.

Still further, according to this invention, the above objects are achieved by a catalyst component for polymerization of olefins being a finely divided aluminoxane comprising an aluminoxane represented by formula [I] or [II]

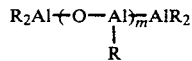

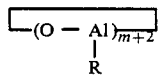

wherein R denotes a hydrocarbon group having 1 to 10 carbon atoms and m denotes an integer of 2 to 50, and having an average particle size of 5 to 200 μm and a specific surface area of 20 to 1,000 m²/g.

DETAILED DESCRIPTION OF THE PREFERRED EMBODIMENTS

The finely divided aluminoxane of this invention comprises an aluminoxane represented by formula [I] or [II]:

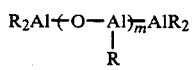

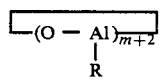

In the above formula, R is a hydrocarbon group having 1 to 10, preferably 1 to 4 carbon atoms. Concrete Examples thereof includes methyl, ethyl, propyl, isopropyl, isopropenyl, n-butyl, sec-butyl, tert-butyl, pentyl, hexyl, octyl, decyl, dodecyl, tridecyl, tetradecyl, hexadecyl, octadecyl, eicosyl, cyclohexyl, cyclooctyl, phenyl, tolyl and ethylphenyl groups. Of these, the methyl, ethyl and isobutyl groups are preferable, and the methyl group is most preferable. m is 2 to 50, preferably 6 to 40, most preferably 10 to 30. The aluminoxane may be a halogenated aluminoxane in which in formula [I] or [II]), part of R is substituted with a halogen atom such as chlorine or bromine and the halogen content is not more than 40% by weight.

In the aluminoxane of formula [I] or [II], oxyaluminum units of formula

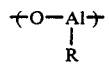

constituting the aluminoxane may be composed of mixed oxyaluminum units containing different hydrocarbon groups. On this occasion, the aluminoxane is preferably an aluminoxane containing at least an oxymethylaluminum unit of formula

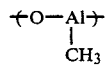

in an amount of preferably at least 30 mole %, more preferably at least 50 mole %, most preferably at least 70 mole %.

The average particle size of the finely divided aluminoxane in this invention is 5 to 200 μm, preferably 10 to 100 μm, most preferably 20 to 60 μm, and the specific surface area thereof is 20 to 1,000 m²/g, preferably 50 to 500 m²/g, most preferably 100 to 300 m²/g. Where the average particle size of the finely divided aluminoxane is less than 5 μm, the bulk specific gravity is high when it is used as a catalyst for polymerization of olefins, making impossible the formation of olefin polymers having excellent properties as a powder. Where said average particle size is larger than 200 μm, a large amount of coarse polymer particles results when it is used as a catalyst component for polymerization of olefins, inviting troubles such as clogging of a polymer discharge outlet or a polymer transportation line. Where the specific surface area of the finely divided aluminoxane is less than 20 m$^2$/g, the polymerization activity decreases less than 20 m when it is used as a catalyst component for polymerization of olefins.

The average particle size of the finely divided aluminoxane here referred to is measured by an optical microscope and determined as an average value of particle sizes found from at least 50 particles optionally selected. The specific surface area of the finely divided aluminoxane is found by utilizing adsorption and desorption on the surface of the powder based on a theory of a BET one point method. On this occasion, a helium/nitrogen (70/30) gas mixture is used as a measuring gas.

A density of the finely divided aluminoxane is 0.5 to 2 g/ml, preferably 0.7 to 1.7 g/ml, most preferably 0.9 to 1.5 g/ml.

Moreover, in this invention, a ratio of the finely divided aluminoxane dissolved in n-hexane held at 25° C. meets a range of usually, 0 to 40 mole %, preferably 0 to 20 mole %, most preferably 0 to 10 mole %.

The ratio of the finely divided aluminoxane dissolved in n-hexane is found by adding 2 g of the finely divided aluminoxane to 50 ml of n-hexane held at 25° C., then stirring the mixture for 2 hours, separating a solution portion by a G-4 glass filter, and measuring an aluminum concentration of the filtrate. Accordingly, the dissolved ratio is determined as a ratio of an aluminum atom present in the filtrate to an amount of an aluminum atom corresponding to 2 g of the aluminoxane used.

The aluminoxane of formula [I] or [II] constituting the finely divided aluminoxane in this invention can be produced by a hitherto known method. Examples of the method are mentioned below.

(1) A method wherein one or more trialkylaluminums are added to a a hydrocarbon solvent suspension of a compound containing an adsorption water or a crystal water-containing salt such as magnesium chloride hydrate, copper sulfate hydrate, aluminum sulfate hydrate, nickel sulfate hydrate or cerous chloride hydrate.

(2) A method wherein one or more trialkylaluminums are directly reacted with water in a medium such as benzene, toluene, ethyl ether or tetrahydrofuran.

Of these methods, the method (1) is preferable. By the way, said aluminoxane may contain a small amount of an organometallic component. A component of an organometallic compound such as a halogen-containing organoaluminum compound or an organomagnesium compound may be present besides the trialkylaluminum.

As a process for producing a finely divided aluminoxane in this invention, there can be employed a process which comprises contacting a solution of the aluminoxane with an aluminoxane-insoluble or -sparingly soluble solvent to precipitate a finely divided solid aluminoxane in suspension. More particularly, it is also possible to employ a process which comprises adding an aluminoxane-insoluble or -sparingly soluble solvent to an aluminoxane solution to contact them, or adding an aluminoxane solution to an aluminoxane-insoluble or -sparingly soluble solvent to contact them with stirring, and thereby precipitating a finely divided solid aluminoxane in suspension, or as required, removing the solvent used to dissolve the aluminoxane from the resulting mixture obtained by the above contact via distillation or flash distillation to prompt precipitation of the finely divided solid aluminoxane.

In contacting the aluminoxane solution with the aluminoxane-insoluble or -sparingly soluble solvent, the ratio of the aluminoxane to the aluminoxane-insluble or -sparingly soluble solvent is usually 10 to 10,000 parts by weight, preferably 100 to 1,000 parts by weight per 100 parts by weight of the aluminoxane. The contacting temperature is usually −100° C. to 300° C., preferably −50° C. to 100° C., most preferably −30° C. to 50° C. The contacting is usually conducted with stirring. In the process of this invention, the aluminoxane solution is formed from at least an aluminoxane and an aluminoxane dissolving solvent. As a method for obtaining the aluminoxane solution, there can be enumerated a method wherein both components are simply mixed and a method wherein they are mixed under heating. An amount of a solvent in the aluminoxane solution is 0.1 to 50 liters, preferably 0.2 to 10 liters, more preferably 0.3 to 2 liters per gram-atom of aluminum in the aluminoxane.

Examples of the solvent of aluminoxane include aromatic hydrocarbons such as benzene, toluene, ethylbenzene, propylbenzene, butylbenzene, xylene and chlorobenzene.

Examples of the aluminoxane-insoluble or -sparingly soluble solvent are generally saturated hydrocarbon solvents, e.g. linear or branched aliphatic hydrocarbons such as pentane, hexane, decane, dodecane, kerosene and cyclohexane, and alicyclic hydrocarbons such as cyclohexane, norbornane and ethyl cyclohexane.

It is advisable that a solvent having a higher boiling point than the solvent employed to obtain the aluminoxane solution is used as an aluminoxane-insoluble or -sparingly soluble solvent.

As a process for producing a finely divided aluminoxane in this invention, there can be employed a process wherein the aluminoxane solution is spray dried to obtain the finely divided aluminoxane. More particularly, the finely divided aluminoxane can be formed by spraying the aluminoxane solution via a spray dryer having a two-fluid nozzle concurrently with an inert gas heated at a temperature usually 10° to 500° C., preferably 50° to 200° C. higher than the boiling point of the solvent while keeping the aluminoxane solution at a temperature usually 2° to 100° C., preferably 5° to 50° C. lower than the boiling point of the solvent. The aluminoxane solution used in this process is the same as mentioned above.

The finely divided aluminoxane of this invention is used as a catalyst component for polymerization of olefins. Among others, the finely divided solid catalyst formed from the finely divided aluminoxane catalyst component and the catalyst component of the compound of the transition metal of Group IVB in the periodic table in this invention has the feature that it has an extremely high polymerization activity even if applied to polymerization or copolymerization of olefins by any of dissolving polymerization, suspension polymerization and gaseous phase polymerization, and that even in suspension polymerization or gaseous phase polymerization, said catalyst shows a very high activity, making possible the formation of polymers having a high specific gravity, thus being excellent in properties as a powder.

Examples of the method using the catalyst component for polymerization of olefins comprising the finely divided aluminoxane in this invention are as follows.

[1] A method which comprises feeding a finely divided aluminoxane component and a component of a compound of a transition metal of Group IVB in the periodic table to a reaction system, forming a catalyst having a polymerization activity in the reaction system, and polymerizing or copolymerizing olefins.

[2] A method which comprises preparing a catalyst wherein a component of a compound of a transition metal of Group IVB in the periodic table is supported on a finely divided aluminoxane component, and polymerizing or copolymerizing olefins in the presence of said catalyst.

As the method [2] for preparing the catalyst wherein the component of the compound of the transition metal of Group IVB in the periodic table is supported on the finely divided aluminoxane component, there can be employed a method wherein the component of the compound of the transition metal of Group IVB in the periodic table is supported on the finely divided aluminoxane once prepared or a method wherein the component of the compound of the transition metal of Group IVB is added in the step of forming the finely divided aluminoxane component, and after the formation of the finely divided aluminoxane a solid catalyst is made wherein the component of the compound of the transition metal of Group IVB in the periodic table is supported on the finely divided aluminoxane. The following two methods (1) and (2) can be shown as a method for producing a solid catalyst for polymerization of olefins wherein the component of the compound of the transition metal of Group IVB in the periodic table is supported on the finely divided aluminoxane component. These methods are described in detail in the patent applications Applicant was filed on December 27, 1986 and Feb. 4, 1987.

(1) A method for producing a solid catalyst for polymerization of olefins which comprises contacting an aluminoxane solution with an aluminoxane-insoluble or -sparingly soluble solvent to precipitate a finely divided solid aluminoxane in suspension and form a suspension of the finely divided solid aluminoxane, and contacting the suspension of the finely divided solid aluminoxane with the solution of the compound of the transition metal of Group IVB in the periodic table to form a solid component.

(2) A method for producing a solid catalyst for polymerization of olefins which comprises spray drying an aluminoxane solution to form a finely divided solid aluminoxane, contacting the finely divided solid aluminoxane with the solution of the compound of the transition metal of Group IVB in the periodic table in the presence of an aluminoxane-insoluble or -sparingly soluble solvent to form a solid component.

Of these methods, the method (1) can afford a polymer having very good properties as a powder. In both the methods (1) and (2), a component such as an electron donor compound to be later described may be added in any of the steps.

The solid catalyst for polymerization of olefins is prepared by the method (1) or (2), and both the methods go though the step of precipitating the aluminoxane or the step of spray drying the aluminoxane. Unless impairing the properties of the finely divided aluminoxane to precipitate and spray dry the aluminoxane, the method can be performed in the presence of trialkylaluminum such as triisobutylaluminum or triisoamylalminum.

The solid catalyst for polymerization of olefins obtained by the above method (1) or (2) comprises at least

[A] a component of a compound of a transition metal of Group IVB in the periodic table and '[B] an aluminoxane catalyst component, a ratio (M/Al) of a transition metal atom (M) to an aluminum metal atom (Al) being 0.2 to 0.001, an average particle size being 5 to 200 $\mu$m and a specific surface area being 20 to 1,000 $m^2/g$.

The catalyst for polymerization of olefins obtained by the above methods may contain a component of an electron donor in addition to [A] the catalyst component of the compound of the transition metal and [B] the aluminoxane catalyst component. Examples of the electron donor include carboxylic acids, esters, ethers, ketones, aldehydes, alcohols, phenols, acid amides, oxygen-containing compounds such as metal atom (aluminum or silicon)—O—C bond-containing compounds, nitriles, amines and phosphines. The content of the electron donor is usually 0 to 1 mole, preferably 0 to 0.6 mole per gram-atom of the transition metal atom (M).

In the solid catalyst for polymerization of olefins, the ratio of the transition metal atom to the aluminum metal atom is 0.2 to 0.001, preferably 0.05 to 0.002, more preferably 0.02 to 0.005. Where the ratio is higher than 0.2, the polymerization activity of the catalyst much decreases. Where the ratio is lower than 0.001, the polymerization activity based on the aluminum atom decreases.

The average particle size of the above solid catalyst for polymerization of olefins is 5 to 200 $\mu$m, preferably 10 to 100 $\mu$m, more preferably 20 to 60 $\mu$m. The average particle size of said solid catalyst for polymerization of olefins is measured by an optical microscope and determined as an average value of particle sizes found from at least 50 particles optionally selected.

When the average particle size is less than 5 $\mu$m, a large amount of a finely divided polymer is formed in a polymer obtained by gaseous phase polymerization or slurry polymerization using the solid catalyst for polymerization of olefins in this invention, and the bulk specific gravity of the polymer is not satisfactorily great, making it impossible to obtain a polymer excellent in properties as a powder. Meanwhile, when the average particle size is larger than 200 $\mu$m, large amounts of coarse polymer particles are formed in the obtained polymer, causing troubles such as clogging of a polymer particle discharge outlet. Moreover, the specific surface area of the solid catalyst for polymerization of olefins in this invention is 20 to 1,000 $m^2/g$, preferably 50 to 500 $m^2/g$, more preferably 100 to 300 $m^2/g$. When the specific surface area is less than 20 $m^2/g$, the polymerization activity of the catalyst tends to notably decrease.

The specific surface area of the solid catalyst for polymerization of olefins here referred to is found by utilizing adsorption and desorption of gas on the surface of a powder based on a theory of a BET one point method. A helium/nitrogen (70/30) gas mixture can be taken as a measuring gas.

In the catalyst component [A], the transition metal of Group IVB in the periodic table is selected from the group consisting of titanium, zirconium and hafnium. Titanium and zirconium are preferable as the transition metal in the catalyst component [A], and zirconium is most preferable.

A zirconium compound in which a group having a conjugated π-electron is a ligand can be taken as an example of the compound of the transition metal of Group IVB in the periodic table in the catalyst component [A].

The zirconium compound in which the group having a conjugated π-electron is a ligand can be, for example, a compound represented by formula (I)

$$R^1{}_k R^2{}_l R^3{}_m R^4{}_n Zr \qquad (I)$$

wherein $R^1$ denotes a cycloalkadienyl group, $R^2$, $R^3$ and $R^4$ each denote a cycloakladienyl, aryl, alkyl, cycloalkyl or aralkyl group, halogen, hydrogen, $OR^a$, $SR^b$, $NR_2{}^c$ or $PR_2{}^d$, $R^a$, $R^b$, $R^c$ and $R^d$ each denote a hydrocarbon group such as an alkyl, cycloalkyl, aryl or aralkyl group, or a silyl group, $R^c$ and $R^d$ may together form a ring, $k \geq 1$ and $k+l+m+n=4$.

Examples of the cycloalkadienyl group include cyclopentadienyl, methylcyclopentadienyl, ethylcyclopentadienyl, dimethylcyclopentadienyl, indenyl and tetrahydroindenyl groups. Examples of the alkyl group include methyl, ethyl, propyl, isopropyl, butyl, hexyl, octyl, 2-ethylhexyl, decyl and oleyl groups. Examples of the aryl group include phenyl and tolyl groups. Examples of the aralkyl group include benzyl and neophyl groups. Examples of the cycloalkyl group include cyclopentyl, cyclohexyl, cyclooctyl, norbonyl and bicyclononyl groups and alkyl substituents of these groups. Besides, unsaturated aliphatic groups such as vinyl, allyl, propenyl, isopropenyl and 1-butenyl groups and unsaturated alicyclic groups such as a cyclohexenyl group are also available. Examples of the halogen include fluorine, chlorine and bromine. Examples of the zirconium compound are as follows.

bis(cyclopentadienyl)zirconium monochloride monohydride,
bis(cyclopentadienyl)zirconium monobromide monohydride,
bis(cyclopentadienyl)methylzirconium hydride,
bis(cyclopentadienyl)ethylzirconium hydride,
bis(cyclopentadienyl)cyclohexylzirconium hydride,
bis(cyclopentadienyl)phenylzirconium hydride,
bis(cyclopentadienyl)benzylzirconium hydride,
bis(cyclopentadienyl)neopentylzirconium hydride,
bis(methylcyclopentadienyl)zirconium monochloride monohydride,
bis(indenyl)zirconium monochloride monohydride,
bis(cyclopentadienyl)zirconium dichloride
bis(cyclopentadienyl)zirconium dibromide,
bis(cyclopentadienyl)methylzirconium monochloride,
bis(cyclopentadienyl)ethylzirconium monochloride,
bis(cyclopentadienyl)cyclohexylzirconium monochloride,
bis(cyclopentadienyl)phenylzirconium monochloride,
bis(cyclopentadienyl)benzylzirconium monochloride,
bis(methylcyclopentadienyl)zirconium dichloride,
bis(pentamethylcyclopentadienyl)zirconium dichloride,
bis(indenyl)zirconium dichloride,
bis(indenyl)zirconium dibromide,
bis(cyclopentadienyl)zirconium diphenyl,
bis(cyclopentadienyl)zirconium dibenzyl,
bis(cyclopentadienyl)methoxyzirconium chloride,
bis(cyclopentadienyl)methoxyzirconium chloride,
bis(cyclopentadienyl)ethoxyzirconium chloride,
bis(cyclopentadienyl)butoxyzirconium chloride,
bis(cyclopentadienyl)2-ethylhexoxyzirconium chloride,
bis(cyclopentadienyl)methylzirconium ethoxide,
bis(cyclopentadienyl)methylzirconium butoxide,
bis(cyclopentadienyl)ethylzirconiuim ethoxide,
bis(cyclopentadienyl)phenylzirconium ethoxide,
bis(cyclopentadienyl)benzylzirconium ethoxide,
bis(methylcyclopentadienyl)ethoxyzirconium chloride,
bis(indenylethoxy)zirconium chloride,
bis(cyclopentadienyl)ethoxyzirconium,
bis(cyclopentadienyl)butoxyzirconium,
bis(cyclopentadienyl)2-ethylhexoxyzirconium,
bis(cyclopentadienyl)phenoxyzirconium chloride,
bis(cyclopentadienyl)cyclohexoxyzirconium chloride,
bis(cyclopentadienyl)phenylmethoxyzirconium chloride,
bis(cyclopentadienyl)methylzirconium phenylmethoxide,
bis(cyclopentadienyl)trimethylsiloxyzirconium chloride,
bis(cyclopentadienyl)triphenylsiloxyzirconium chloride,
bis(cyclopentadienyl)thiophenylzirconium chloride,
bis(cyclopentadienyl)thioethylzirconium chloride,
bis(cyclopentadienyl)bis(dimethylamide)zirconium,
bis(cyclopentadienyl)diethylamidezirconium chloride,
ethylenebis(indenyl)ethoxyzirconium chloride,
ethylenebis(4,5,6,7-tetrahydro-1-indenyl)ethoxyzirconium chloride,
ethylenebis(indenyl)dimethylzirconium,
ethylenebis(indenyl)diethylzirconium,
ethylenebis(indenyl)diphenylzirconium,
ethylenebis(indenyl)dibenzylzirconium,
ethylenebis(indenyl)methylzirconium monobromide,
ethylenebis(indenyl)ethylzirconium monochloride,
ethylenebis(indenyl)benzylzirconium monochloride,
ethylenebis(indenyl)methylzirconium monochloride,
ethylenebis(indenyl)zirconium dichloride,
ethylenebis(indenyl)zirconium dibromide,
ethylenebis(4,5,6,7-tetrahydro-1-indenyl)-dimethylzirconium,
ethylenebis(4,5,6,7-tetrahydro-1-indenyl)-methylzirconium monochloride,
ethylenebis(4,5,6,7-tetrahydro-1-indenyl)-zirconium dichloride,
ethylenebis(4,5,6,7-tetrahydro-1-indenyl)-zirconium dibromide,
ethylenebis(4-methyl-1-indenyl)zirconium dichloride,
ethylenebis(5-methyl-1-indenyl)zirconium dichloride,
ethylenebis(6-methyl-1-indenyl)zirconium dichloride,
ethylenebis(7-methyl-1-indenyl)zirconium dichloride,
ethylenebis(5-methoxy-1-indenyl)zirconium dichloride,
ethylenebis(2,3-dimethyl-1-indenyl)zirconium dichloride,
ethylenebis(4,7-dimethyl-1-indenyl)zirconium dichloride,
ethylenebis(4,7-dimethoxy-1-indenyl)zirconium dichloride,
ethylenebis(indenyl)zirconium dimethoxide,
ethylenebis(indenyl)zirconium diethoxide,
ethylenebis(indenyl)methoxyzirconium chloride, ethylenebis(indenyl)ethoxyzirconium chloride,
ethylenebis(indenyl)methylzirconium ethoxide,
ethylenebis(4,5,6,7-tetrahydro-l-indenyl)-zirconium dimethoxide,
ethylenebis(4,5,6,7-tetrahydro-l-indenyl)-zirconium diethoxide,
ethylenebis(4,5,6,7-tetrahydro-l-indenyl)-methoxyzirconium chloride,
ethylenebis(4,5,6,7-tetrahydro-l-indenyl)-ethoxyzirconium chloride, and
ethylenebis(4,5,6,7-tetrahydro-l-indenyl)-methylzirconium ethoxide.

Examples of the titanium compound are mentioned below.
bis(cyclopentadienyl)titanium monochloride monohydride,
bis(cyclopentadienyl)methyltitanium hydride,
bis(cyclopentadienyl)phenyltitanium chloride,
bis(cyclopentadienyl)benzyltitanium chloride,
bis(cyclopentadienyl)titanium chloride,
bis(cyclopentadienyl)titanium dibenzyl,
bis(cyclopentadienyl)ethoxytitanium chloride,
bis(cyclopentadienyl)butoxytitanium chloride,
bis(cyclopentadienyl)methyltitanium ethoxide,
bis(cyclopentadienyl)phenoxytitanium chloride,
bis(cyclopentadienyl)trimethylsiloxytitanium chloride,
bis(cyclopentadienyl)thiophenyltitanium chloride,
bis(cyclopentadienyl)bis(dimethylamide)titanium,
bis(cyclopentadienyl)ethoxytitanium,
ethylenebis(indenyl)titanium dichlride, and
ethylenebis(4,5,6,7-tetrahydro-l-indenyl)titanium dichloride.

Examples of the hafnium compound are mentioned below.
bis(cyclopentadienyl)hafnium monochloride monohydride,
bis(cyclopentadienyl)ethylhafnium hydride,
bis(cyclopentadienyl)phenylhafnium chloride,
bis(cyclopentadienyl)hafnium dichlride,
bis(cyclopentadienyl)hafnium dibenzyl,
bis(cyclopentadienyl)ethoxyhafnium chloride,
bis(cyclopentadienyl)butoxyhafnium chloride,
bis(cyclopentadienyl)methylhafniuim ethoxide,
bis(cyclopentadienyl)phenoxyhafnium chloride,
bis(cyclopentadienyl)thiophenylhafnium chloride,
bis(cyclopentadienyl)bis(diethylamide)hafnium,
ethylenebis(indenyl)hafnium dichloride, and
ethylenebis(4,5,6,7-tetrahydro-l-indenyl)hafnium dichloride.

The above solid catalyst for polymerization of olefins is effective for producing olefin polymers, above all, an ethylene polymer and an ethylene/alpha-olefin copolymer. Examples of olefins that can be polymerized in the presence of the catalyst in this invention include alpha-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, 1-octadecene and 1-eicosene. Of these, polymerization of ethylene or copolymerization of ethylene and an alpha-olefin having 3 to 10 carbon atoms is preferable.

In the polymerization using the above solid catalyst for polymerization of olefins, olefins are polymerized usually in a gaseous phase or in slurry. In the slurry polymerization, either inactive hydrocarbons or the olefins per se can be used as a solvent.

Concrete examples of the hydrocarbon solvent include aliphatic hydrocarbons such as butane, isobutane, pentane, hexane, octane, decane, dodecane, hexadecane and octadecane, alicyclic hydrocarbons such as cyclopentane, methylcyclopentane, cyclohexane and cyclooctane, and petroleum fractions such as kerosene and light oils.

When performing the slurry polymerization of olefins using the above solid catalyst for polymerization of olefins, the temperature is usually −50° C. to 120° C., preferably 0° to 100° C.

When performing the gaseous phase polymerization of olefins using the above solid catalyst for polymerization of olefins, the polymerization temperature is usually 0° to 120° C., preferably 20° to 100° C.

At the time of using the solid catalyst for polymerization of catalysts in the slurry polymerization or the gaseous phase polymerization, the proportion of the transition metal compound is usually to $10^{-8}$ to $10^{-2}$ gram-atom/liter, preferably $10^{-7}$ to $10^{-3}$ gram-atom/liter as a concentration of the transition metal atom in the polymerization reaction system.

In the above polymerization reaction, the aluminoxane may also be used in combination with an organoaluminum compound represented by formula

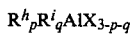

$$R^h_p R^i_q AlX_{3-p-q}$$

wherein $R^h$ denotes a hydrocarbon group having 1 to 10, preferably 1 to 6 carbon atoms, an alkenyl group, a cycloalkyl group or an aryl group, $R^i$ denotes an alkoxy group having 1 to 6 carbon atoms or an aryloxy group, X denotes a halogen atom, $3 \geq p > 0$ and $2 \geq q \geq 0$. Especially, the addition of the organoaluminum compound having a branched chain group such as triisobutylaluminum or isoprenylaluminum is effective for improving the polymerization activity.

The polymerization pressure is usually a normal pressure to 100 kg/cm², preferably an increased pressure of 2 to 50 kg/cm². The polymerization can be performed batchwise, semi-continuously or continuously. Further, the polymerization can also be carried out by dividing it into two or more stages different in reaction conditions.

In the olefin polymerization, it is advisable to conduct prepolymerization of olefins in the presence of the solid catalyst prior to the olefin polymerization. The prepolymerization is carried out by polymerizing an alpha-olefin in an amount of 1 to 1000 g, preferably 5 to 500 g, more preferably 10 to 200 g per 1 milligram-atom of [A] the catalyst component of the compound of the transition metal of Group IVB in the periodic table. Examples of the olefins used in the prepolymerization include ethylene and alpha-olefins having 3 to 20 carbon atoms, such as propylene, 1-butene, 4-methyl-1-pentene, 1-hexene, 1-octene, 1-decene, 1-dodecene and 1-tetradecene. Ethylene or ethylene and a small amount of the alpha-olefin are preferable.

The temperature of the prepolymerization is −20° C. to 70° C., preferably −10° C. to 60° C., more preferably 0° C. to 50° C.

The prepolymerization can be conducted batchwise or continuously under normal pressure or increased pressure. In the prepolymerization, a molecular weight modifier such as hydrogen may be present. It is advisable to control the amount of said modifier such that a pre polymer having an intrinsic viscosity [η], measured at 135° C. in decalin, of at least 0.2 dl/g, preferably 0.5 to 20 dl/g can be prepared.

The prepolymerization is effected in the absence of a solvent or in an inert hydrocarbon solvent. It is desirous to conduct the prepolymerization in the inert hydrocarbon solvent in the aspect of operability. The aforesaid examples of the aluminoxane-insoluble or -sparingly soluble solvent can be taken as the inert hydrocarbon solvent used in the prepolymerization.

In the prepolymerization, the concentration of the solid catalyst in the prepolymerization reaction system is usually $10^{-6}$ gram-atom/liter, preferably $10^{-4}$ to $10^{-2}$ gram-atom/liter.

This invention can provide the finely divided aluminoxane having the large specific surface area and the uniform particle size, and the process for producing same. By using the finely divided aluminoxane as the catalyst component, the solid catalyst for polymerization of olefins showing the very high polymerization activity in homopolymerization or copolymerization of olefins is obtained which can produce the polymers and copolymers having the high bulk specific gravity and the uniform particle size, containing less fine powder and having the narrow molecular weight distribution and the narrow composition distribution in case of the copolymers.

EXAMPLES

The following Examples illustrate this invention in more detail.

Synthesis of aluminoxane

A 400-milliliter glass flask equipped with a stirrer which was thoroughly purged with nitrogen was charged with 37 g of $Al_2(SO_4)_3.14\ H_2O$ and 125 ml of toluene. After the mixture was cooled to 0° C., 125 ml of toluene containing 50 ml of trimethylaluminum was added dropwise over the course of 1 hour. Subsequently, the temperature was elevated to 40° C. for 3 hours, and the reaction continued at that temperature for 48 hours. After the reaction, a solid/liquid separation was conducted by filtration. Low-boiling substances were removed from the separated liquid by means of an evaporator. Toluene was added to the remaining solid which was collected as a toluene solution.

The molecular weight found from freezing point depression in benzene was 884, and the degree of polymerization of the aluminoxane was therefore 15.

EXAMPLE 1

[Preparation of finely divided aluminoxane]

A 300-milliliter reactor fitted with a stirrer, capable of pressure reduction, was charged with 67 ml of a toluene solution containing 100 millimoles, as aluminum atom, of the above methylaluminoxane. Thereafter, 100 ml of purified n-decane was added at room temperature over the course of about 0.5 hour under stirring to precipitate methylaluminoxane. Subsequently, while reducing the pressure of the inside of the reactor to 4 torr through a vacuum pump, the temperature of the inside of the reactor was raised to 35° C. over the course of about 3 hours to remove toluene in the reactor and further precipitate methylaluminoxane. The reaction liquid was filtered by a filter to remove the liquid portion. There resulted a finely divided aluminoxane. Said finely divided aluminoxane had the average particle size of 29 μm, the specific surface area of 168 $m^2$/g and the ratio of it dissolved in n-hexane of 25° C. of 1.3 mole %.

[Preparation of a solid catalyst]

The finely divided aluminoxane was resuspended in n-decane and 5 ml of a toluene solution containing 0.2 millimoles of bis(cyclopentadienyl)zirconium dichloride was added thereto. After mixing them at room temperature for about 1 hour, the liquid phase portion was removed by a filter. There resulted a solid catalyst for polymerization of olefins.

The solid catalyst had the zirconium content of 0.6% by weight and the aluminum content of 47% by weight, and the average particle size found by observation of a microscope was about 30 μm. The specific surface area was 171 $m^2$/g, and the density was 1.18 g/ml.

[Prepolymerization]

A 400-milliliter reactor fitted with a stirrer was charged in an atmosphere of nitrogen with 100 ml of purified n-decane and 0.1 millimole, as zirconium atom, of the above solid catalyst, followed by feeding ethylene for 1 hour at a rate of 4 Nl/hr. During this time, the temperature was kept at 20° C. After feeding of ethylene was over, the inside of the reactor was purged with nitrogen and then washed once with purified hexane. The product was resuspended in hexane and stored in a catalyst bottle.

[Polymerization]

A 2-liter autoclave thoroughly purged with nitrogen was charged with 250 g of sodium chloride as a dispersant. While heating it at 90° C., the pressure reduction was conducted for 2 hours by a vacuum pump such that the internal pressure of the autoclave became 50 mmHg or less. The temperature of the autoclave was then lowered to 75° C., and the inside of the autoclave was replaced with ethylene. Subsequently, 0.01 millimole, as zirconium atom, of the solid catalyst subjected to the prepolymerization was added, and the autoclave was then closed. 50 Nml of hydrogen was added and the pressure was increased with ethylene such that the internal pressure of the autoclave reached 8 kg/$cm^2$G. The stirring rate was increased to 300 rpm, and the polymerization was conducted at 80° C. for 1 hour.

After the polymerization was finished, the total amounts of the polymer and sodium chloride in the autoclave was taken out, and charged into about 1 liter of water. By stirring for about 5 minutes, almost the total amount of sodium chloride was dissolved in water, and the polymer alone floated on the surface of water. The floating polymer was recovered, thoroughly washed with methanol and dried overnight at 80° C. in vacuo. The amount of the resulting polymer was 147.8 g. Said polymer had MFR of 0.9 dg/min, the apparent bulk density of 0.44 g/ml and $\overline{M}w/\overline{M}n$ of 2.5.

COMPARATIVE EXAMPLE 1

In Example 1, purified n-decane was not added to a toluene solution containing methylaluminoxane, and while the pressure of the inside of the reactor was reduced to 4 torr with the vacuum pump, the temperature of the inside of the reactor was elevated to 35° C. over the course of about 3 hours to remove toluene in the reactor and precipitate methylaluminoxane. The specific surface area of the thus obtained solid aluminoxane was 1.2 $m^2$/g. When the particles of said solid aluminoxane were observed by a microscope, the particle size was 1 to 100 μm. Thus, the size and shape thereof were non-uniform. This solid aluminoxane was suspended in n-decane and zirconium was supported thereon as in Example 1 to form a solid catalyst. The solid catalyst had the zirconium content of 0.6% by weight and the aluminum content of 48% by weight.

In the same way as in Example 1, prepolymerization and gaseous phase polymerization of ethylene were conducted. The results are shown in Table 1.

EXAMPLE 2

Example 1 was repeated except that the solvent used to dissolve bis(cyclopentadienyl)zirconium chloride was changed from toluene to 1,2-dichloroethane. There resulted a finely divided aluminoxane. Said finely divided aluminoxane had the average particle size of 30 μm area of 162 m$^2$/g. The ratio of and the specific surface the finely divided aluminoxane dissolved in n-hexane of 25° C. was 1.1 mole %. Using the finely divided aluminoxane, a solid catalyst was prepared as in Example 1, and prepolymerization and gaseous phase polymerization of ethylene were performed as in Example 1. The results are shown in Table 1.

EXAMPLE 3

Example 1 was repeated except that the solvent used to dissolve methylaluminoxane was changed from toluene to ethylbenzene. Consequently, a finely divided aluminoxane was obtained. Said finely divided aluminoxane had the average particle size of 30 μm and the specific surface area of 168 m$^2$/g. The ratio of the finely divided aluminoxane dissolved in n-hexane of 25° C. was 2.2 mole %. In the same way as in Example 1, a solid catalyst was prepared from said finely divided aluminoxane, and prepolymerization and gaseous phase polymerization of ethylene were conducted. The results are shown in Table 1.

EXAMPLE 4

Ethylene and hexene-1 were copolymerized by gaseous phase polymerization. That is, using the solid catalyst subjected to prepolymerization described in Example 1, the copolymerization of ethylene and hexene-1 was performed as in Example 1 except that 10 ml of hexene-—1 was added after the addition of the catalyst component and the polymerization time was shortened from 1 hour to 20 minutes. The results are shown in Table 2.

EXAMPLE 5

Slurry polymerization was carried out using the solid catalyst in Example 1. Namely, a 2-liter autoclave thoroughly replaced with ethylene was charged with 450 g of liquefied isobutane, and the temperature was elevated to 60° C. After adding 0.008 millimole, as zirconium atom, of the solid catalyst component subjected to prepolymerization described in Example 1, 80 ml of 4-methyl-1-pentene and 50 Nml of hydrogen were added. Subsequently, ethylene was introduced to keep the internal pressure of the autoclave at 3.5 kg/cm$^2$ for 1 hour. During this time, the temperature was adjusted to 70° C. One hour later, about 2 ml of methanol was added to the autoclave and the polymerization was completely stopped, followed by releasing the pressure. The obtained polymer was recovered and dried overnight at 80° C. in vacuo. The amount of the resulting polymer was 216.7 g. Said polymer had MFR of 0.8 dg/min., the apparent bulk density of 0.42 g/ml, the density of 0.912 g/ml and $\overline{M}w/\overline{M}n$ of 2.8.

EXAMPLE 6

Three hundred milliliters of a toluene solution containing 500 millimoles, as aluminum atom, of methylaluminoxane was sprayed concurrently with hot nitrogen of 120° C. using a spray dryer having a two-fluid nozzle with a spray nozzle 0.25 mm in diameter while keeping it at 50° C. As a result, toluene was evaporated and aluminoxane solid particles were obtained. The finely divided aluminoxane had the average particle size of 46 μm and the specific surface area of 130 m$^2$/g. To a suspension comprising 5.8 g of the resulting aluminoxane particles and 100 ml of n-decane was added 5 ml of a toluene solution containing 0.2 millimole of bis(cyclopentadienyl)zirconium dichloride with stirring. After they were mixed at room temperature for about 1 hour, a liquid phase portion was removed by a filter In consequence, a solid catalyst for polymerization of olefins was obtained.

The solid catalyst had the zirconium content of 0.6% by weight and the aluminum content of 46% by weight. The average catalyst particle size found by observation of a microscope was about 47 μm. The specific surface area was 126 m$^2$/g. Prepolymerization and gaseous phase polymerization of ethylene were carried out as in Example 1. The results are shown in Table 1.

EXAMPLE 7

A solid catalyst was prepared as in Example 1 except that the amount of bis(cyclopentadienyl)zirconium dichloride was changed from 0.2 millimole to 0.33 millimole. Prepolymerization and gaseous phase polymerization were carried out as in Example 1. The results are shown in Table 2.

EXAMPLE 8

A solid catalyst was prepared as in Example 1 except that the amount of bis(cyclopentadienyl)zirconium dichloride was changed from 0.2 millimole to 0.5 millimole. Prepolymerization and gaseous phase polymerization were carried out as in Example 1. The results are shown in Table 2.

EXAMPLE 9

Gaseous phase polymerization of ethylene was performed as in Example 8 except that 1.3 millimoles of triisobutylaluminum was added just before the addition of the solid catalyst component subjected to prepolymerization. The results are shown in Table 2.

TABLE 1

|  | Catalyst composition (wt. %) | | Catalyst particle size | Specific surface area | Polymerization method | Polymerization activity | Apparent bulk density |
| --- | --- | --- | --- | --- | --- | --- | --- |
|  | Zr | Al | μm | m$^2$/g |  | g-PE/mM Zr | g/cm$^3$ |
| Example 1 | 0.6 | 47 | 30 | 171 | Gaseous phase | 14,000 | 0.44 |
| Comparative | 0.6 | 48 | 1–100 | 1.2 | Gaseous | 2,200 | unmeasurable |

TABLE 1-continued

| | Catalyst composition (wt. %) | | Catalyst particle size μm | Specific surface area m²/g | Polymerization method | Polymerization activity g-PE/mM Zr | Apparent bulk density g/cm³ |
|---|---|---|---|---|---|---|---|
| | Zr | Al | | | | | |
| Example 1 | | | | | phase | * | (less than 0.1) |
| Example 2 | 0.6 | 46 | 28 | 168 | Gaseous phase | 14,000 | 0.44 |
| Example 3 | 0.6 | 47 | 31 | 165 | Gaseous phase | 13,600 | 0.43 |

TABLE 2

| | Catalyst composition (wt. %) | | Catalyst particle size μm | Specific surface area m²/g | Polymerization method | Polymerization activity g-PE/mM Zr | Apparent bulk density g/cm³ | Density g/cm³ |
|---|---|---|---|---|---|---|---|---|
| | Zr | Al | | | | | | |
| Example 4 | 0.6 | 47 | 30 | 171 | Gaseous phase | 10,100 | 0.41 | 0.918 |
| Example 5 | 0.6 | 47 | 30 | 171 | Slurry | 27,100 | 0.42 | 0.912 |
| Example 6 | 0.6 | 46 | 47 | 126 | Gaseous phase | 8,100 | 0.40 | — |
| Example 7 | 0.9 | 46 | 31 | 158 | Gaseous phase | 16,300 | 0.45 | — |
| Example 8 | 1.1 | 45 | 31 | 163 | Gaseous phase | 10,700 | 0.43 | — |
| Example 9 | 1.1 | 45 | 31 | 163 | Gaseous phase | 14,300 | 0.44 | — |

EXAMPLE 10

Preparation of finely divided aluminoxane)

A 300-milliliter reactor fitted with a stirrer, capable of pressure reduction, was charged with 67 ml of a toluene solution containing 100 millimoles, as aluminum atom, of the above methylaminoxane, and 100 ml of purified n-decane was added at room temperature over the course of about 0.5 hour with stirring to precipitate methylaluminoxane. Subsequently, while reducing the pressure of the inside of the reactor to 4 torr by a vacuum pump, the temperature of the inside of the reactor was raised to 35° C. for about 3 hours to remove toluene in the reactor and further precipitate methylaluminoxane. The reaction liquid was filtered via a filter. After a liquid phase portion was removed, a solid portion was resuspended in about 60 ml of hexane and the suspension was moved to a catalyst bottle. The finely divided aluminoxane had the average particle size of 29 μm and the specific surface area of 168 m²/g. The ratio of the finely divided aluminoxane dissolved in n-hexane of 25° C. was 1.3 mole %.

[Polymerization]

A 2-liter autoclave thoroughly replaced with ethylene was charged with 1 liter of purified n-decane, and the temperature was elevated to 45° C. After adding 0.06 ml of a 1,2-dichloroethane solution containing 3 millimoles, as aluminum atom, of the above finely divided aluminoxane and 0.010 millimole of bis(cyclopentadienyl)-zirconium dichloride, the temperature was raised to 80° C., ethylene was introduced, and the pressure was increased to 8 kg/cm²G. Thus, polymerization was performed for 1 hour. There resulted 87 g of a polyethylene powder.

What is claimed is:

1. A finely divided aluminoxane comprising an aluminoxane represented by formula [I] or [II]

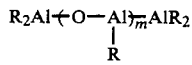

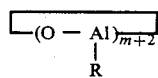

wherein R denotes a hydrocarbon group having 1 to 10 carbon atoms and m denotes an integer of 2 to 50, an average particle size being 5 to 200 μm and a specific surface area being 20 to 1,000 m²/g.

2. The finely divided aluminoxane of claim 1 comprising an aluminoxane represented by formula [I] or [II]

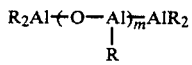

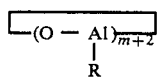

wherein R denotes a hydrocarbon group having 1 to 4 carbon atoms and m denotes an integer of 6 to 40, an average particle size being 10 to 100 μm and a specific surface area being 50 to 500 m²/g.

3. The finely divided aluminoxane of claim 2 wherein a density of the finely divided aluminoxane is 0.7 to 1.7 g/ml.

4. The finely divided aluminoxane of claim 2 wherein a density of the finely divided aluminoxane is 0.9 to 1.5 g/ml.

5. The finely divided aluminoxane of claim 2 wherein the aluminoxane of formula [I] or [II] is methylaluminoxane or an aluminoxane composed of mixed oxyaluminum units of formula

containing at least an oxymethylaluminum unit of formula

6. The finely divided aluminoxane of claim 3 wherein the aluminoxane of formula [I] or [II] is methylaluminoxane or an aluminoxane composed of mixed oxyaluminum units of formula

containing at least an oxymethylaluminum unit of formula

7. The finely divided aluminoxane of claim 4 wherein the aluminoxane of formula [I] or [II] is methylaluminoxane or an aluminoxane composed of mixed oxyaluminum units of formula

containing at least an oxymethylaluminum unit of formula

8. The finely divided aluminoxane of claim 1 wherein in formula [I] or [II] R is a methyl group and m is an integer of 10 to 30, an average particle size is 20 to 60 $\mu$m, a specific surface area is 100 to 300 m$^2$/g and a density is 0.9 to 1.5 g/ml.

9. A process for producing a finely divided aluminoxane which comprises contacting a solution of an aluminoxane represented by formula [I] or [II]

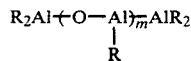

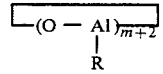

wherein R denotes a hydrocarbon group having 1 to 10 carbon atoms and m denotes an integer of 2 to 50,
with an aluminoxane-insoluble or -sparingly soluble solvent to precipitate a finely divided solid aluminoxane in suspension.

10. The process of claim 9 which comprises contacting a solution of an aluminoxane represented by formula [I] or [II]

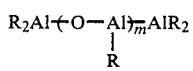

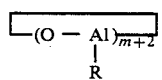

wherein R denotes a hydrocarbon group having 1 to 4 carbon atoms and m denotes an integer of 6 to 40, with an aluminoxane-insoluble or -sparingly soluble solvent to precipitate a finely divided solid aluminoxane in suspension.

11. The process of claim 9 wherein the resulting finely divided solid aluminoxane has an average particle size of 10 to 100 $\mu$m and a specific surface area of 50 to 500 m$^2$/g.

12. The process of claim 10 wherein the resulting finely divided solid aluminoxane has an average particle size of 10 to 100 $\mu$m and a specific surface area of 50 to 500 m$^2$/g.

13. The process of claim 11 wherein the resulting finely divided solid aluminoxane has a density of 0.7 to 1.7 g/ml.

14. The process of claim 12 wherein the resulting finely divided solid aluminoxane has a density of 0.7 to 1.7 g/ml.

15. The process of claim 9 wherein an aliphatic or alicyclic hydrocarbon is used as the aluminoxane-insoluble or -sparingly soluble solvent.

16. The process of claim 10 wherein an aliphatic or alicyclic hydrocarbon is used as the aluminoxane-insoluble or -sparingly soluble solvent.

17. The process of claim 9 wherein the aluminoxane of formula [I] or [II] is methylaluminoxane or an aluminoxane composed of mixed oxyaluminum units of formula

containing at least an oxymethylaluminum unit of formula

18. The process of claim 10 wherein the aluminoxane of formula [I] or [II] is methylaluminoxane or an aluminoxane composed of mixed oxyaluminum units of formula

containing at least an oxymethylaluminum unit of formula

19. The process of claim 9 wherein the aluminoxane-insoluble or -sparingly soluble solvent is used in an amount of 10 to 10,000 parts by weight per 100 parts by weight of the solution of aluminoxane.

20. The process of claim 10 wherein the aluminoxane-insoluble or -sparingly soluble solvent is used in an amount of 10 to 10,000 parts by weight per 100 parts by weight of the solution of aluminoxane.

21. The process of claim 9 which comprises contacting a solution of an aluminoxane of formula [I] or [II] wherein R is a methyl group and m is an integer of 10 to 30 with an aluminoxane-insoluble or -sparingly soluble solvent to precipitate a finely divided solid aluminoxane in suspension.

22. A process for producing a finely divided aluminoxane which comprises spray drying a solution of an aluminoxane represented by formula [I] or [II]

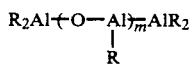 [I]

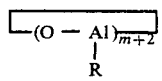 [II]

wherein R denotes a hydrocarbon group having 1 to 10 carbon atoms and m denotes an integer of 6 to 50, to form a finely divided solid aluminoxane.

23. The process of claim 22 which comprises spray drying a solution of an aluminoxane represented by formula [I] or [II]

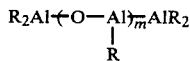 [I]

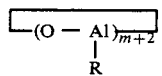 [II]

wherein R denotes a hydrocarbon group to 4 carbon atoms and m denotes an integer of 6 to 40, to form a finely divided solid aluminoxane.

24. The process of claim 22 wherein the resulting finely divided solid aluminoxane has an average particle size of 10 to 100 μm and a specific surface area of 50 to 500 m²/g.

25. The process of claim 23 wherein the resulting finely divided solid aluminoxane has an average particle size of 10 to 100 μm and a specific surface area of 50 to 500 m²/g.

26. The process of claim 24 wherein the resulting finely divided solid aluminoxane has a density of 0.7 to 1.7 g/ml.

27. The process of claim 25 wherein the resulting finely divided solid aluminoxane has a density of 0.7 to 1.7 g/ml.

28. The process of claim 22 wherein the solution of the aluminoxane is sprayed using an inert gas heated at a temperature 10° to 500° C. higher than the boiling point of the solvent by means of a two-fluid nozzle maintained at a temperature 5° to 50° C. lower than the boiling point of the solvent.

29. The process of claim 23 wherein the solution of the aluminoxane is sprayed using an inert gas heated at a temperature 10° to 500° C. higher than the boiling point of the solvent by means of a two-fluid nozzle maintained at a temperature 5° to 50° C. lower than the boiling point of the solvent.

30. The process of claim 22 wherein the aluminoxane of formula [I] or [II] is methylaluminoxane or an aluminoxane composed of mixed oxyaluminum units of formula

containing at least an oxymethylaluminum unit of formula

31. The process of claim 23 wherein the aluminoxane of formula [I] or [II] is methylaluminoxane or an aluminoxane composed of mixed oxyaluminum units of formula

containing at least an oxymethylaluminum unit of formula

32. The process of claim 22 which comprises spray drying a solution of an aluminoxane represented by formula [I] or [II]

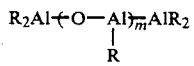 [I]

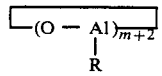 [II]

wherein R denotes a methyl group and m denotes an integer of 10 to 30, to form a finely divided solid aluminoxane.

* * * * *

UNITED STATES PATENT AND TRADEMARK OFFICE
CERTIFICATE OF CORRECTION

PATENT NO. : 4,952,540

DATED : August 28, 1990

INVENTOR(S) : KIOKA, ET AL.

It is certified that error appears in the above-identified patent and that said Letters Patent is hereby corrected as shown below:

Column 23, line 49;

Claim 23, line 6, between "group" and "to", insert --1--.

Signed and Sealed this

Twenty-first Day of July, 1992

Attest:

DOUGLAS B. COMER

Attesting Officer

Acting Commissioner of Patents and Trademarks